United States Patent
Piedimonte et al.

(10) Patent No.: US 6,562,335 B1
(45) Date of Patent: May 13, 2003

(54) NK-1 RECEPTOR ANTAGONISTS FOR PREVENTION OF NEUROGENIC INFLAMMATION IN GENE THERAPY

(75) Inventors: Giovanni Piedimonte, Miami, FL (US); Hans J. Hess, Old Lyme, CT (US); John A. Lowe, III, Stonington, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/077,045

(22) Filed: May 18, 1998

Related U.S. Application Data

(63) Continuation of application No. PCT/IB96/01042, filed on Oct. 2, 1996.
(60) Provisional application No. 60/005,002, filed on Oct. 10, 1995, and provisional application No. 60/006,344, filed on Nov. 7, 1995.

(51) Int. Cl.$^7$ .............................................. A61K 48/00
(52) U.S. Cl. .................... 424/93.2; 514/44; 514/527.5; 435/320.1
(58) Field of Search ................................ 514/44, 527.5; 536/23.5; 530/402; 435/325; 424/93.2

(56) References Cited

U.S. PATENT DOCUMENTS

| | | | |
|---|---|---|---|
| 5,744,480 A | | 4/1998 | Lowe, III et al. ............ 514/329 |
| 5,773,450 A | | 6/1998 | Lowe, III et al. ............ 514/329 |
| 5,872,154 A | * | 2/1999 | Wilson et al. ............... 514/885 |
| 5,993,800 A | * | 11/1999 | Linsley et al. ............ 424/93.21 |
| 6,048,859 A | * | 4/2000 | Dorn et al. ................ 514/227.5 |

FOREIGN PATENT DOCUMENTS

| | | |
|---|---|---|
| CA | 2160462 | 11/1994 |
| WO | 94-26735 | * 11/1994 |
| WO | 9507908 | 3/1995 |

OTHER PUBLICATIONS

Appell et al., "Antagonists that demonstrate species differences in neurokinin–1 receptors." Molecular Pharmacology, vol. 41 (4): 772–8, Apr. 1992.*
Jiang et al., "Cellular heterogeneity of CFTR expression and function in the lung: implications for gene therapy of cystic fibrosis." European J. of Human Genetics, vol. 6(1): 12–31, Jan. 1998.*
Eck et al., "Gene–Based Therapy." Goodman &Gilman's The Pharmacological Basis of Therapeutics—Ninth Edition, McGraw Hill: 77–101, 1996.*
Boucher, Current status of CF gene therapy, Mar. 1996, TIG, vol. 12, No. 3, pp. 81–84.*
Gunzburg et al., Virus vector design in gene therpy,1995, Molecular Medcine Today, pp. 410–417.*
Anderson, Human gene therpy, Apr. 30, 1998, Nature, vol. 392, pp. 25–30.*
Verma et al., Gene therpy–promises, problems and propects, Sep. 18, 1997, Nature, vol. 389, pp. 239–242.*
Merck & Co. Inc, Tachykinin antagonists, 1994, Ashley Publications, vol. 4, pp. 859–860.*
Felten et al., Nordrenergic and peptidergic innervation of secondary lymphoid organs: roles in experimental rheumatiod arthrits, 1992, European Journal of Clinical Investigation, vol. 22, No. 1, pp. 37–41.*
Neil et al., Substance P but Not Vasoactive Intestinal Peptide Modulates Immunoglobulin Secretion in Murine Schistosomiasis, 1991, Cellular Immunology, vol. 135, pp. 394–401.*
Rameshwar et al., Stimulation of IL–2 Production in Murine Lymhphocytes by Sustance P and Related Tachykinins, Sep. 1, 1993, The Journal of Immunology, vol. 151, No. 5, pp. 2484–2496.*
Yoshihara, S., et al. "Plasma Extravasation in the Rat Trachea Induced by Cold Air Is Mediated by Tachykinin Release from Sensory Nerves." American Journal of Respiratory and Critical Care Medicine, vol. 151, No. 4 (1995) pp. 1011–1017. (XP 00616240).
Rodger, Ian W., et al. "Neurokinin Receptors Subserving Plasma Extravasation in Guinea Pig Airways." Can J. Physio. Pharmacol., vol. 73, (1995) pp. 927–931. (XP 000615879).
Piedimonte, G., et al. "NK–1 receptors mediate neurogenic inflammatory increase in blood flow in rat airways." J. Appl. Physio., vol. 74, No. 5 (1993) pp. 2462–2468 (XP 000615897).
Maggi, C. A. "Tachykinin receptors and airway pathophysiology." Cur. Respir. J., vol. 6, No. 5 (1993) pp. 735–742. (XP 00615882).
Kudlacz, E. M., et al. "Parainfluenza virus type 3 induced alterations in tachykinin NK–1 receptors, substance P levels and respiratory functions in guinea pig airways." European Journal of Pharmacology Env. Toxicol., vol. 270, No. 4 (1994) pp. 291–300. (XP 000615929).
Germonpre, P. R., et al. "Characterization of the Neurogenic Plasma Extravasation in the Airways." Arch, Int. Pharmacodyn, vol. 329, No. 1 (1995) pp. 185–203. (XP 000615899).
Piedimonte, G. et al. "Adenoviral Vector–Induced Potentiation of Airway Neurogenic Inflation is reduced. But not Abolished by UV–Psoralen Inactivation" (1995) Cystic Fibrosis Conference.

* cited by examiner

Primary Examiner—Dave Trong Nguyen
(74) Attorney, Agent, or Firm—Ladas & Parry

(57) ABSTRACT

The present invention relates to a method for inhibiting a neurogenic inflammation caused or potentiated by an administration of viral vectors in gene therapy by administering to said mammal an antagonist that binds to a NK-1 receptor in an amount that is effective to inhibit said neurogenic inflammation.

6 Claims, No Drawings

NK-1 RECEPTOR ANTAGONISTS FOR PREVENTION OF NEUROGENIC INFLAMMATION IN GENE THERAPY

This application is a continuation of PCT application IB 96/01042 filed on Oct. 2, 1996. This application claims the benefit under 35 USC 119(e) of U.S. Patent Applications No. 60/005,002 filed on Oct. 10, 1995 and No. 60/006,344 filed on Nov. 7, 1995.

The present invention relates to the use of NK-1 receptor antagonists (e.g., substance P receptor antagonists) to prevent or treat the neurogenic inflammation associated with the use of viral vectors in gene therapy.

The administration of vectors bearing genetic constructs useful in gene therapy has been associated with induction of a neurogenic inflammatory response. This neurogenic response is caused by the local release of substance P and other peptide neurotransmitters from unmyelinated C-fibers around airway microvessels. The present inventors believe that antagonists of the NK-1 receptor, through which substance P and other tachykinins mediate their biological responses, will inhibit this inflammation and thus be useful therapeutically. Controlling the neurogenic inflammatory response, for example, in the airways after inhalation of an appropriate adenovirus vector, will allow for subsequent pursuit of the gene therapy protocol.

SUMMARY OF THE INVENTION

The present invention relates to a method of preventing or treating the neurogenic inflammation caused or potentiated by the administration of viral vectors in gene therapy in a mammal, including a human, comprising administering to such mammal an amount of an NK-1 receptor antagonist that is effective in preventing or treating such neurogenic inflammation.

A more specific embodiment of this invention relates to the above method wherein the neurogenic inflammation being prevented or treated is that caused or potentiated by the administration of adenoviral vectors in gene therapy.

Another more specific embodiment of this invention relates to the above methods wherein the neurogenic inflammation that is being prevented or treated is the pulmonary inflammation and edema caused or potentiated by endotracheal inoculation with an adenoviral vector carrying a genetic construct used in gene therapy.

Another more specific embodiment of this invention relates to the embodiment described immediately above, wherein the genetic construct comprises the gene to correct the defective chloride ion transporter in patients with cystic fibrosis.

Other more specific embodiments of this invention relate to the above methods wherein the NK-1 receptor antagonist is selected from the group consisting of:

(2S,3S)-3-(5-tert-butyl-2-methoxybenzyl)amino-2-(3-trifluoromethoxyphenyl)piperidine;
(2S,3S)-3-(2-isopropoxy-5-trifluoromethoxybenzyl)amino-2-phenyl-piperidine;
(2S,3S)-3-(2-ethoxy-5-trifluoromethoxybenzyl)amino-2-phenyl-piperidine;
(2S,3S)-3-(2-methoxy-5-trifluoromethoxybenzyl)-amino-2-phenylpiperidine;
(2S,3S)-3(-5-tert-butyl-2-trifluoromethoxybenzyl)amino-2-phenylpiperidine;
2-(diphenylmethyl)-N-(2-methoxy-5-trifluoromethoxyphenyl)methyl-1-azabicyclo[2.2.2]octan-3-amine;
(2S,3S)-3-[5-chloro-2-(2,2,2-trifluoroethoxy)-benzyl]amino-2-phenylpiperidine;
(2S,3S)-3-(-5-tert-butyl-trifluoromethoxybenzyl)amino-2-phenylpiperidine;
(2S,3S)-3-(2-isopropoxy-5-trifluoromethoxybenzyl)amino-2-phenylpiperidine;
(2S,3S)-3-(2-difluoromethoxy-5-trifluoromethoxybenzyl)-amino-2-phenylpiperidine;
(2S,3S)-2-phenyl-3-[2-(2,2,2-trifluoroethoxybenzyl)-aminopiperidine;
(2S,3S)-2-phenyl-3-(2-trifluoromethoxybenzyl)]aminopiperidine;
cis-3-(2-chlorobenzylamino)-2-phenylpiperidine;
cis-3-(2-trifluoromethylbenzylamino)-2-phenylpiperidine;
cis-3-(2-methoxybenzylamino)-2-(2-fluorophenyl)piperidine;
cis-3-(2-methoxybenzylamino)-2-(2-chlorophenyl)piperidine;
cis-3-(2-methoxybenzylamino)-2-(2-methylphenyl)piperidine;
cis-3-(2-methoxybenzylamino)-2-(3-methoxyphenyl)piperidine;
cis-3-(2-methoxybenzylamino)-2-(3-fluorophenyl)piperidine;
cis-3-(2-methoxybenzylamino)-2-(3-chlorophenyl)piperidine;
cis-3-(2-methoxybenzylamino)-2-(3-methylphenyl)-piperidine;
cis-3-(2-methoxybenzylamino)-2-(4-fluorophenyl)-piperidine;
cis-3-(2-methoxybenzylamino)-2-(3-thienyl)-piperidine;
cis-3-(2-methoxybenzylamino)-2-phenylazacyclo-heptane;
3-(2-methoxybenzylamino)-4-methyl-2-phenylpiperidine;
3-(2-methoxybenzylamino)-5-methyl-2-phenylpiperidine;
(2S,3S)-1-(5-carboethoxypent-1-yl)-3-(2-methoxybenzyl-amino)-2-phenylpiperidine;
(2S,3S)-1-(6-hydroxy-hex-1-yl)-3-(2-methoxybenzyl-amino)-2-phenylpiperidine;
(2S,3S)-1-(4-hydroxy-4-phenylbut-1-yl)-3-(2-methoxybenzylamino)-2-phenylpiperidine;
(2S,3S)-1-(4-oxo-4-phenylbut-1-yl)-3-(2-methoxybenzyl-amino)-2-phenylpiperidine;
(2S,3S)-1-(5,6-dihydroxyhex-1-yl)-3-(2-methoxybenzyl-amino)-2-phenylpiperidine;
cis-3-(5-fluoro-2-methoxybenzylamino)-2-phenyl-piperidine;
(2S,3S)-1-[4-(4-fluorophenyl)-4-oxobut-1-yl]-3-(2-methoxybenzylamino)-2-phenylpiperidine;
(2S,3S)-1-[4-[4-fluorophenyl)-4-hydroxybut-1-yl]-3-(2-methoxybenzylamino)-2-phenylpiperidine;
cis-3-(2-methoxy-5-methylbenzylamino)-2-phenyl-piperidine;
(2S,3S)-1-(4-benzamidobut-1-yl)-3-(2-methoxybenzyl-amino)-2-phenylpiperidine;
cis-3-(2-methoxynaphth-1-ylmethylamino)-2-phenyl-piperidine;
(2S,3S)-3-(2-methoxybenzylamino)-1-(5-N-methyl-carboxamidopent-1-yl)-2-phenylpiperidine;
(2S,3S)-1-(4-cyanobut-1-yl)-3-(2-methoxybenzylamino)-2-phenylpiperidine;
(2S,3S)-1-[4-(2-naphthamido)but-1-yl]-3-(2-methoxy-benzylamino)-2-phenylpiperidine;
(2S,3S)-1-(5-benzamidopent-1-yl)-3-(2-methoxybenzyl-amino)-2-phenylpiperidine;
(2S,3S)-1-(5-aminopent-1-yl)-3-(2-methoxybenzylamino)-2-phenylpiperidine;
(2S,3S)-3-(5-chloro-2-methoxybenzylamino)-2-phenyl-piperidine;
(2S,3S)-3-(2,5-dimethoxybenzylamino)-2-phenyl-piperidine;

cis-3-(3,5-difluoro-2-methoxybenzylamino)-2-phenyl-piperidine;
cis-3-(4,5-difluoro-2-methoxybenzylamino)-2-phenyl-piperidine;
cis-3-(2,5-dimethoxybenzylamino)-1-[4-(4-fluorophenyl)-4-oxobut-1-yl]-2-phenylpiperidine;
cis-3-(5-chloro-2-methoxybenzylamino)-1-(5,6-dihydroxyhex-1-yl)-2-phenylpiperidine;
cis-1-(5,6-dihydroxyhex-1-yl)-3-(2,5-dimethoxy-benzylamino)-2-phenylpiperidine;
cis-2-phenyl-3-[-2(prop-2-yloxy)benzylamino]piperidine;
cis-3-(2,5-dimethoxybenzyl)amino-2-(3-methoxy-phenyl)piperidine hydrochloride;
cis-3-(5-chloro-2-methoxybenzyl)amino-2-(3-methoxy-phenyl)piperidine dihydrochloride;
cis-3-(5-chloro-2-methoxybenzyl)amino-2-(3-chloro-phenyl)piperidine dihydrochloride;
3-(2-methoxybenzylamino)-2,4-diphenylpiperidine;
(2S,3S)-3-(2-methoxybenzylamino)-2-phenylpiperidine;
cis-3-(2-methoxybenzylamino)-2-phenylpyrrolidine;
(2S,3S)-3-(5-ethyl-2-methoxybenzyl)amino-2-phenyl-piperidine;
(2S,3S)-3-(5-n-butyl-2-methoxybenzyl)amino-2-phenyl-piperidine;
(2S,3S)-3-(2-methoxy-5-n-propylbenzyl)amino-2-phenyl-piperidine;
(2S,3S)-3-(5-isopropyl-2-methoxybenzyl)amino-2-phenyl-piperidine;
(2S,3S)-3-(5-s-butyl-2-methoxybenzyl)amino-2-phenyl-piperidine;
(2S,3S)-3-(5-t-butyl-2-methoxybenzyl)amino-2-phenyl-piperidine;
(2S,3S)-3-(2-methoxy-5-phenylbenzyl)amino-2-phenyl-piperidine;
2,4-dimethylthiazole-5-sulfonic acid[4-methoxy-3-((2S,3S)-2-phenylpiperidin-3-ylaminomethyl)phenyl]-methylamide;
N-(4,5-dimethylthiazol-2-yl)-N-[4-methoxy-3-((2S,3S)-2-phenylpiperidin-3-yl-aminomethyl)phenyl]-methanesulfonamide;
{5[(4,5-dimethylthiazol-2-yl)methylamino]-2-methoxybenzyl}-((2S,3S)-2-phenylpiperidin-3-yl)amine;
{5-(4,5-dimethylthiazol-2-ylamino)-2-methoxybenzyl}-((2S,3S)-2-phenylpiperidin-3-ylamine;
4,5-dimethylthiazole-2-sulfonic acid methyl-[3-((2S,3S)-2-phenylpiperidin-3-ylaminomethyl)-4-trifluoromethoxyphenyl]-amide;
2,4-dimethylthiazole-5-sulfonic acid[4-isopropoxy-3-((2S,3S)-2-phenylpiperidin-3-ylaminomethyl)phenyl]-methylamide;
2,4-dimethylthiazole-5-sulfonic acid[4-isopropoxy-3-((2S,3S)-2-phenylpiperidin-3-ylaminomethyl)phenyl]-isopropylamide;
2,4-dimethylthiazole-5-sulfonic acid[4-methoxy-3-((2S,3S)-2-phenylpiperidin-3-ylaminomethyl)phenyl]-isopropylamide;
2,4-dimethylthiazole-5-sulfonic acid[4-methoxy-3-((2S,3S)-2-phenylpiperidin-3-ylaminomethyl)phenyl]-isobutylamide;
2,4-dimethylthiazole-5-sulfonic acid[4-isopropoxy-3-((2S,3S)-2-phenylpiperidin-3-ylaminomethyl)phenyl]-isobutylamide;
(2S,3S)-N-(5-isopropyl-2-methoxyphenyl)methyl-2-diphenylmethyl-1-azabicyclo[2.2.2]octan-3-amine;
(2S,3S)-N-(5-tert-butyl-2-methoxyphenyl)methyl-2-diphenylmethyl-1-azabicyclo[2.2.2]octan-3-amine;
(2S,3S)-N-(5-methyl-2-methoxyphenyl)methyl-2-diphenylmethyl-1-azabicyclo[2.2.2]octan-3-amine;
(2S,3S)-N-(5-ethyl-2-methoxyphenyl)methyl-2-diphenylmethyl-1-azabicyclo[2.2.2]octan-3-amine;
(2S,3S)-N-(5-isopropyl-2-methoxyphenyl)methyl-2-diphenylmethyl-1-azabicyclo[2.2.2]octan-3-amine;
(2S,3S)-N-(5-sec-butyl-2-methoxyphenyl)methyl-2-diphenylmethyl-1-azabicyclo[2.2.2]octan-3-amine;
(2S,3S)-N-(5-n-propyl-2-methoxyphenyl)methyl-2-diphenylmethyl-1-azabicyclo[2.2.2]octan-3-amine;
(2S,3S)-2-diphenylmethyl-3-(5-tert-butyl-2-methoxybenzyl)amino-1-azabicyclo[2.2.2]octane;
(2S,3S)-N-[5-(1-cyano-1-methylethyl)-2-methoxybenzyl]-2-phenylpiperidine-3-amine;
(2S,3S)-3-(6-methoxy-1-methyl-2-oxo-1,2,3,4-tetrahydroquinolin-7-yl)methyl-2-phenylpiperidine-3-amine;
(2S,3S)-2-phenyl-N-[5-[2,2,2-trifluoro-1-(trifluoromethyl)ethyl]-2-methoxybenzyl]piperidine-3-amine;
(2S,3S)-2-diphenylmethyl-N-[2-methoxy-5-(methylsulfonyl)benzyl]-1-azabicyclo[2.2.2]octane-3-amine;
(2S,3S)-2-diphenylmethyl-N-(5-isopropenyl-2-methoxybenzyl)-1-azabicyclo[2.2.2]octane-3-amine;
(2S,3S)-2-diphenylmethyl-N-[5-(1-hydroxy-1-methylethyl)-2-methoxybenzyl]-1-azabicyclo[2.2.2]octane-3-amine;
(3R,4S,5S,6S)-N,N-diethyl-5-(5-isopropyl-2-methoxy-benzylamino)-6-diphenylmethyl-1-azabicyclo[2.2.2]octane-3-carboxamide;
(3R,4S,5S,6S)-N,N-diethyl-5-(2,5-dimethoxybenzylamino)-6-diphenylmethyl-1-azabicyclo[2.2.2]octane-3-carboxamide;
(3R,4S,5S,6S)-5-(5-isopropyl-2-methoxybenzylamino)-6-diphenylmethyl-1-azabicyclo[2.2.2]octane-3-carboxylic acid;
(3R,4S,5S,6S)-5-(2-methoxy-2-methylthiobenzylamino)-6-diphenylmethyl-1-azabicyclo[2.2.2]octane-3-carboxylic acid;
(3R,4S,5S,6S)-5-(2,5-dimethoxybenzylamino)-6-phenyl-methyl-1-azabicyclo[2.2.2]octane-3-carboxylic acid;
(3R,4S,5S,6S)-5-(2-methoxy-5-methylbenzylamino)-6-diphenylmethyl-1-azabicyclo[2.2.2]octane-3-carboxylic acid;
(3R,4S,5S,6S)-5-(5-ethyl-2-methoxybenzylamino)-6-diphenylmethyl-1-azabicyclo[2.2.2]octane-3-carboxylic acid;
(3R,4S,5S,6S)-5-(2-methoxyl-5-n-propylbenzylamino)-6-diphenylmethyl-1-azabicyclo[2.2.2]octane-3-carboxylic acid;
(3R,4S,5S,6S)-5-(5-sec-butyl-2-methoxybenzylamino)-6-diphenylmethyl-1-azabicyclo[2.2.2]octane-3-carboxylic acid;
(3R,4S,5S,6S)-5-(5-N-methyl-methanesulfonylamino-2-methoxy-benzylamino)-6-diphenylmethyl-1-azabicyclo[2.2.2]octane-3-carboxylic acid;
(3R,4S,5S,6S)-5-(2-methoxy-5-methylsulfinylbenzyl-amino)-6-phenylmethyl-1-azabicyclo[2.2.2]octane-3-carboxylic acid;
(3R,4S,5S,6S)-5-(2-methoxy-5-trifluoromethoxybenzyl-amino)-6-diphenylmethyl-1-azabicyclo[2.2.2]octane-3-carboxylic acid;
(3R,4S,5S,6S)-5-(2-methoxy-5-methylsulfonylbenzyl-amino)-6-diphenylmethyl-1-azabicyclo[2.2.2]octane-3-carboxylic acid;
(3R,4S,5S,6S)-5-(5-dimethylamino-2-methoxybenzylamino)-6-diphenylmethyl-1-azabicyclo[2.2.2]octane-3-carboxylic acid;
(3R,4S,5S,6S)-5-(5-isopropyl-2-methoxybenzylamino)-6-diphenylmethyl-1-azabicyclo[2.2.2]octane-2-carboxylic acid;

(3R,4S,5S,6S)-5-(2-methoxy-5-methylthiobenzylamino)-6-diphenylmethyl-1-azabicyclo[2.2.2]octane-2-carboxylic acid;

(3R,4S,5S,6S)-5-(2,5-dimethoxybenzylamino)-6-diphenylmethyl-1-azabicyclo[2.2.2]octane-2-carboxylic acid;

(3R,4S,5S,6S)-5-(2-methoxy-5-methylbenzylamino)-6-diphenylmethyl-1-azabicyclo[2.2.2]octane-2-carboxylic acid;

(3R,4S,5S,6S)-5-(5-ethyl-2-methoxybenzylamino)-6-diphenylmethyl-1-azabicyclo[2.2.2]octane-2-carboxylic acid;

(3R,4S,5S,6S)-5-(2-methoxyl-5-n-propylbenzylamino)-6-diphenylmethyl-1-azabicyclo[2.2.2]octane-2-carboxylic acid;

(3R,4S,5S,6S)-5-(5-sec-butyl-2-methoxybenzylamino)-6-diphenylmethyl-1-azabicyclo[2.2.2]octane-2-carboxylic acid;

(3R,4S,5S,6S)-5-(5-N-methyl-methanesulfonylamino-2-methoxybenzyl-amino)-6-phenylmethyl-1-azabicyclo[2.2.2]octane-2-carboxylic acid;

(3R,4S,5S,6S)-5-(2-methoxy-5-methylsulfinylbenzyl-amino)-6-phenylmethyl-1azabicyclo[2.2.2]octane-2-carboxylic acid;

(3R,4S,5S,6S)-5-(2-methoxy-5-trifluoromethoxybenzyl-amino)-6-diphenylmethyl-1-azabicyclo[2.2.2]octane-2-carboxylic acid;

(3R,4S,5S,6S)-5-(2-methoxy-5-methylsufonylbenzyl-amino)-6-phenylmethyl-1-azabicyclo[2.2.2]octane-2-carboxylic acid; and (3R,4S,5S,6S)-5-(5-dimethylamino-2-methoxybenzylamino)-6-diphenylmethyl-1-azabicyclo[2.2.2]octane-2-carboxylic acid;

and the pharmaceutically acceptable salts of the foregoing compounds.

DETAILED DESCRIPTION OF THE INVENTION

The following references refer, collectively, to quinuclidine, piperidine, ethylene diamine, pyrrolidine and azanorbornane derivatives and related compounds that exhibit activity as NK-1 receptor antagonists and which can be used, in combination with from one to four other active ingredients, as described above, in the pharmaceutical compositions and methods of this invention, and to methods of preparing the same: U.S. Pat. No. 5,162,339, which issued on Nov. 11, 1992; U.S. Pat. No. 5,232,929, which issued on Aug. 3, 1993; World Patent Application WO 92/20676, published Nov. 26, 1992; World Patent Application WO 93/00331, published Jan. 7, 1993; World Patent Application WO 92/21677, published Dec. 10, 1992; World Patent Application WO 93/00330, published Jan. 7, 1993; World Patent Application WO 93/06099, published Apr. 1, 1993; World Patent Application WO 93/10073, published May 27, 1993; World Patent Application WO 92/06079, published Apr. 16,1992; World Patent Application WO 92/12151, published Jul. 23, 1992; World Patent Application WO 92/15585, published Sep. 17, 1992; World Patent Application WO 93/10073, published May 27, 1993; World Patent Application WO 93/19064, published Sep. 30, 1993; World Patent Application WO 94/08997, published Apr. 28, 1994; World Patent Application WO 94/04496, published Mar. 3, 1994; World Patent Application WO 94/13663, published Jun. 23, 1994; World Patent Application WO 94/20500, published Sep. 15, 1994; World Patent Application PCT/IB94/00221, which designates the United States and was filed on Jul. 18, 1994; World Patent Application PCT/JP94/00781, which designates the United States and was filed on May 13, 1994; World Patent Application PCT/JP94/01092, which designates the United States and was filed on Jul. 5, 1994; and World Patent Application PCT/JP94/01514, which designates the United States and was filed on Sep. 13, 1994. All of the foregoing World Patent Applications designate the United States as a national state in which they will be prosecuted. The foregoing patents and patent applications are incorporated herein by reference in their entireties.

The specific NK-1 receptor antagonists listed in the Summary of the Invention can be prepared by methods described in the patents and patent applications listed above and in the scientific literature.

Other NK-1 receptor antagonists that can be used in the combination therapies of this invention are described in the following references: European Patent Application EP 499,313, published Aug. 19, 1992; European Patent Application EP 520,555, published Dec. 30, 1992; European Patent Application EP 522,808, published Jan. 13, 1993, European Patent Application EP 528,495, published Feb. 24, 1993, PCT Patent Application WO 93/14084, published Jul. 22, 1993, PCT Patent Application WO 93/01169, published Jan. 21, 1993, PCT Patent Application WO 93/01165, published Jan. 21, 1993, PCT Patent Application WO 93/01159, published Jan. 21, 1993, PCT Patent Application WO 92/20661, published Nov. 26, 1992, European Patent Application EP 517,589, published Dec. 12, 1992, European Patent Application EP 428,434, published May 22, 1991, European Patent Application EP 360,390, published Mar. 28, 1990, PCT Patent Application WO 95/04042, published Feb. 9, 1995, PCT Patent Application WO 95/08549, published Mar. 30, 1995, PCT Patent Application WO 95/19344, published Jul. 20, 1995, PCT Patent Application WO 95/23810, published Sep. 8, 1995, and PCT Patent Application WO 95/20575, published Aug. 3, 1995. These publications are also incorporated herein by reference in their entireties.

Generally, in carrying out the methods of this invention, the NK-1 receptor antagonist will be administered to an adult human in an amount ranging from about 0.07 to about 21 mg per kg body weight of the subject being treated per day, in single or divided doses, preferably from about 0.36 to about 4.3 mg/kg. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The NK-1 receptor antagonists and their pharmaceutically acceptable salts that are employed in the and methods of this invention are hereinafter also referred to as the "therapeutic agents". The therapeutic agents can be administered via either the oral or parenteral route.

The therapeutic agents may be administered alone or in combination with pharmaceutically acceptable carriers or diluents by either of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, suppositories, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutic compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic agent in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The activity of certain therapeutic agents as substance P receptor antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a $-70°$ C. freezer and homogenized in 50 volumes (w./v.) of an ice-cold 50 mM Tris (i.e., trimethamine which is 2-amino-2-hydroxymethyl-1,3-propanediol)hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 4 µg/ml of bacitracin, 4 µg/ml of leupeptin, 2 µg of chymostatin and 200 µg/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (ca. $20°$ C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The following study was performed to determine whether the exaggerated inflammatory reaction associated with the endotracheal administration of Ad5CMVLacZ can be prevented by selective antagonism of the substance P (NK-1) receptor. Pathogen-free Fischer F344 male rats (220–287 grams in weight, 12–14 weeks of age), under sodium pentobarotal anesthesia, received a localized endotracheal inoculation with 100 µL cf phosphate-buffered saline (PBS) containing $3 \times 10^{12}$ particles/mL of Ad5CMVLacZ, an adenovirus type 5 vector defective in the E1 and E3 regions of the viral genome and containing the LacZ transgene under the control of the CMV (cytomegalo virus) immediate early promoter. A control group of rats was inoculated with sterile PBS. Five days after the inoculation, 2 groups of rats inoculated with the adenoviral vector were pretreated with the selective substance P (NK-1) receptor antagonist (2S, 3S)-2-phenyl-3-[(2-methoxyphenyl)methylamino] piperidine (compound A) (4 mg/kg i.v.; n=5), or with its inactive stereoisomer (2R,3R)-2-phenyl-3-[(2-methoxyphenyl)methylamino]piperidine (compound B) (4 mg/kg i.v.; n=5). Two other groups of rats inoculated with vector (n=6) or with PBS (n=6) did not receive any pretreatment.

Five minutes after pretreatment, Evans blue dye (30 mg/kg i.v.) was injected into all the rats to measure the increase in vascular permeability associated with the neurogenic inflammation. Capsaicin (75 mg/kg i.v. over 2 min) was injected immediately after Evans blue to stimulate the sensory nerves in the airway mucosa. Five minutes after capsaicin, the rats were perfused through the heart with 100 mL of PBS. The trachea and main stem bronchi were removed and incubated in formamide (18 hours at $50°$ C.) to extract the extravasated tracer. The magnitude of the Evans blue extravasation was determined by spectrophotometric measurements of the optical density of formamide extracts.

The extravasation of Evans blue produced by capsaicin in rats inoculated with Ad5CMVLacZ was inhibited by compound A (33.5±4.6 vs. 104.5±5.9 mg/kg, mean ±SEM; p<0.001) but not by compound B (88.3±5.8 ng/mg; p>0.05). After compound A, capsaicin-induced extravasation in vector-inoculated rats was not different from that in PBS-inoculated rats (43.9±4.9 ng/mg; p>0.05).

These results indicate that the potentiation of neurogenic inflammator caused by the exposure of rat airways to Ad5CMVLacZ involves activation of the substance P (NK-1) receptor and can be prevented by the selective antagonism of this receptor.

What is claimed is:

1. A method for inhibiting a neurogenic inflammation caused or potentiated by an administration of viral vectors in gene therapy in a mammal wherein Substance P is a contributory factor in said neurogenic inflammation, said method comprising administering to said mammal an antagonist that binds to a NK-1 receptor which antagonist inhibits binding of substance P to said NK-1 receptor, in an amount that is effective to inhibit said neurogenic inflammation.

2. A method according to claim 1 wherein the neurogenic inflammation being prevented or treated is that caused or potentiated by the administration of adenoviral vectors in gene therapy.

3. A method according to claim 2, wherein the neurogenic inflammation is being inhibited is pulmonary inflammation and edema caused or potentiated by endotracheal inoculation with an adenoviral vector carrying a genetic construct.

4. A method according to claim 3, wherein the genetic construct comprises cystic fibrosis transmembrane regulator gene.

5. A method according to claim 1 wherein the NK-1 receptor antagonist employed is selected from the group consisting of:

(2S,3S)-3-(5-tert-butyl-2-methoxybenzyl)amino-2-(3-trifluoromethoxyphenyl)piperidine;
(2S,3S)-3-(2-isopropoxy-5-trifluoromethoxybenzyl)amino-2-phenyl-piperidine;
(2S,3S)-3-(2-ethoxy-5-trifluoromethoxybenzyl)amino-2-phenyl-piperidine;
(2S,3S)-3-(2-methoxy-5-trifluoromethoxybenzyl)-amino-2-phenylpiperidine;
(2S,3S)-3-(-5-tert-butyl-2-trifluoromethoxybenzyl)amino-2-phenylpiperdine;
2-(diphenylmethyl)-N-(2-methoxy-5-trifluoromethoxyphenyl)methyl-1-azabicyclo[2.2.2]octan-3-amine;
(2S,3S)-3-[5-chloro-2-(2,2,2-trifluoroethoxy)-benzyl]amino-2-phenylpiperdine;
(2S,3S)-3-(5-tert-butyl-2-trifluoromethoxybenzyl)amino-2-phenylpiperidine;
(2S,3S)-3-(2-isopropoxy-5-trifluoromethoxybenzyl)amino-2-phenylpiperidine;
(2S,3S)-3-(2-difluoromethoxy-5-trifluoromethoxybenzyl)-amino-2-phenylpiperidine;
(2S,3S)-2-phenyl-3-[2-(2,2,2-trifluoroethoxybenzyl)-aminopiperidine;
(2S,3S)-2-phenyl-3-(2-trifluoromethoxybenzyl)]aminopiperidine;
cis-3-(2-chlorobenzylamino)-2-phenylpiperidine;
cis-3-(2-trifluoromethylbenzylamino)-2-phenyl-piperidine;
cis-3-(2-methoxybenzylamino)-2-(2-fluorophenyl)-piperidine;
cis-3-(2-methoxybenzylamino)-2-(2-chlorophenyl)-piperidine;
cis-3-(2-methoxybenzylamino)-2-(2-methylphenyl)-piperidine;
cis-3-(2-methoxybenzylamino)-2-(3-methoxyphenyl)-piperidine;
cis-3-(2-methoxybenzylamino)-2-(3-fluorophenyl)-piperidine;
cis-3-(2-methoxybenzylamino)-2-(3-chlorophenyl)-piperidine;
cis-3-(2-methoxybenzylamino)-2-phenylpiperidine;
cis-3-(2-methoxybenzylamino)-2-(3-methylphenyl)-piperidine;
cis-3-(2-methoxybenzylamino)-2-(4-fluorophenyl)-piperidine;
cis-3-(2-methoxybenzylamino)-2-(3-thienyl)-piperidine;
cis-3-(2-methoxybenzylamino)-2-phenylazacyclo-heptane;
(2S,3S)-3-(2-methoxybenzylamino)-2-phenylpiperidine;
3-(2-methoxybenzylamino)-4-methyl-2-phenylpiperidine;
3-(2-methoxybenzylamino)-5-methyl-2-phenylpiperidine;
3-(2-methoxybenzylamino)-6-methyl-2-phenylpiperidine;
(2S,3S)-1-(5-carboethoxypent-1-yl)-3-(2-methoxybenzyl-amino)-2-phenylpiperidine;
(2S,3S)-1-(6-hydroxy-hex-1-yl)-3-(2-methoxybenzyl-amino)-2-phenylpiperidine;
(2S,3S)-1-(4-hydroxy-4-phenylbut-1-yl)-3-(2-methoxy-benzylamino)-2-phenylpiperidine;
(2S,3S)-1-(4-oxo-4-phenylbut-1-yl)-3-(2-methoxybenzyl-amino)-2-phenylpiperidine;
(2S,3S)-1-(5,6-dihydroxyhex-1-yl)-3-(2-methoxybenzyl-amino)-2-phenylpiperidine;
cis-3-(5-fluoro-2-methoxybenzylamino)-2-phenyl-piperidine;
(2S,3S)-1-[4-(4-fluorophenyl)-4-oxobut-1-yl]-3-(2-methoxybenzylamino)-2-phenylpiperidine;
(2S,3S)-1-[4-[4-fluorophenyl)-4-hydroxybut-1-yl]-3-(2-methoxybenzylamino)-2-phenylpiperidine;
cis-3-(2-methoxy-5-methylbenzylamino)-2-phenyl-piperidine;
(2S,3S)-1-(4-benzamidobut-1-yl)-3-(2-methoxybenzyl-amino)-2-phenylpiperidine;
cis-3-(2-methoxynaphth-1-ylmethylamino)-2-phenyl-piperidine;
(2S,3S)-3-(2-methoxybenzylamino)-1-(5-N-methyl-carboxamidopent-1-yl)-2-phenylpiperidine;
(2S,3S)-1-(4-cyanobut-1-yl)-3-(2-methoxybenzylamino)-2-phenylpiperidine;
(2S,3S)-1-[4-(2-naphthamido)but-1-yl]-3-(2-methoxy-benzylamino)-2-phenylpiperidine;
(2S,3S)-1-(5-benzamidopent-1-yl)-3-(2-methoxybenzyl-amino)-2-phenylpiperidine;
(2S,3S)-1-(5-aminopent-1-yl)-3-(2-methoxybenzylamino)-2-phenyl-piperidine;
(2S,3S)-3-(5-chloro-2-methoxybenzylamino)-2-phenyl-piperidine;
(2S,3S)-3-(2,5-dimethoxybenzylamino)-2-phenyl-piperidine;
cis-3-(3,5-difluoro-2-methoxybenzylamino)-2-phenyl-piperidine;
cis-3-(4,5-difluoro-2-methoxybenzylamino)-2-phenyl-piperidine;
cis-3-(2,5-dimethoxybenzylamino)-1-[4-(4-fluorophenyl)-4-oxobut-1-yl]-2-phenylpiperidine;
cis-3-(5-chloro-2-methoxybenzylamino)-1-(5,6-dihydroxyhex-1-yl)-2-phenylpiperidine;
cis-1-(5,6-dihydroxyhex-1-yl)-3-(2,5-dimethoxy-benzylamino)-2-phenylpiperdine;
cis-2-phenyl-3-[-2(prop-2-yloxy)benzylamino]piperidine;
cis-3-(2,5-dimethoxybenzyl)amino-2-(3-methoxy-phenyl) piperidine hydrochloride;
cis-3-(5-chloro-2-methoxybenzyl)amino-2-(3-methoxy-phenyl)piperidine dihydrochloride;
cis-3-(5-chloro-2-methoxybenzyl)amino-2-(3-chloro-phenyl)piperidine dihydrochloride;
3-(2-methoxybenzylamino)-2,4-diphenylpiperidine;
cis-3-(2-methoxybenzylamino)-2-phenylpyrrolidine;
(2S,3S)-3-(5-ethyl-2-methoxybenzyl)amino-2-phenyl-piperidine;
(2S,3S)-3-(5-n-butyl-2-methoxybenzyl)amino-2-phenyl-piperidine;
(2S,3S)-3-(2-methoxy-5-n-propylbenzyl)amino-2-phenyl-piperidine;

(2S,3S)-3-(5-isopropyl-2-methoxybenzyl)amino-2-phenyl-piperidine;

(2S,3S)-3-(5-s-butyl-2-methoxybenzyl)amino-2-phenyl-piperidine;

(2S,3S)-3-(5-t-butyl-2-methoxybenzyl)amino-2-phenyl-piperidine;

(2S,3S)-3-(2-methoxy-5-phenylbenzyl)amino-2-phenyl-piperidine;

2,4-dimethylthiazole-5-sulfonic acid[4-methoxy-3-((2S,3S)-2-phenylpiperidin-3-yl-aminomethyl)phenyl]-methylamide;

N-(4,5-dimethylthiazol-2-yl)-N-[4-methoxy-3-((2S,3S)-2-phenylpiperidin-3-yl-aminomethyl)phenyl]-methanesulfonamide;

{5-[(4,5-dimethylthiazol-2-yl)methylamino]-2-methoxybenzyl}-((2S,3S)-2-phenylpiperidin-3-yl)amine;

{5-(4,5-dimethylthiazol-2-yl-amino)-2-methoxybenzyl}-((2S,3S)-2-phenylpiperidin-3-ylamine;

4,5-dimethylthiazole-2-sulfonic acid methyl-[3-((2S,3S)-2-phenylpiperidin-3-ylaminomethyl)-4-trifluoromethoxyphenyl]-amide;

2,4-dimethylthiazole-5-sulfonic acid[4-isopropoxy-3-((2S,3S)-2-phenylpiperidin-3-ylaminomethyl)phenyl]-methylamide;

2,4-dimethylthiazole-5-sulfonic acid[4-isopropoxy-3-((2S,3S)-2-phenylpiperidin-3-ylaminomethyl)phenyl]-isopropylamide;

2,4-dimethylthiazole-5-sulfonic acid[4-methoxy-3-((2S,3S)-2-phenylpiperidin-3-ylaminomethyl)phenyl]-isopropylamide;

2,4-dimethylthiazole-5-sulfonic acid[4-methoxy-3-((2S,3S)-2-phenylpiperidin-3-ylaminomethyl)phenyl]-isobutylamide;

2,4-dimethylthiazole-5-sulfonic acid[4-isopropoxy-3-((2S,3S)-2-phenylpiperidin-3-ylaminomethyl)phenyl]-isobutylamide;

(2S,3S)-N-(5-isopropyl-2-methoxyphenyl)methyl-2-diphenylmethyl-1-azabicyclo[2.2.2]octan-3-amine;

(2S,3S)-N-(5-tert-butyl-2-methoxyphenyl)methyl-2-diphenylmethyl-1-azabicyclo[2.2.2]octan-3-amine;

(2S,3S)-N-(5-methyl-2-methoxyphenyl)methyl-2-diphenylmethyl-1-azabicyclo[2.2.2]octan-3-amine;

(2S,3S)-N-(5-ethyl-2-methoxyphenyl)methyl-2-diphenylmethyl-1-azabicyclo[2.2.2]octan-3-amine;

(2S,3S)-N-(5-isopropyl-2-methoxyphenyl)methyl-2-diphenylmethyl-1-azabicyclo[2.2.2]octan-3-amine;

(2S,3S)-N-(5-sec-butyl-2-methoxyphenyl)methyl-2-diphenylmethyl-1-azabicyclo[2.2.2]octan-3-amine;

(2S,3S)-N-(5-n-propyl-2-methoxyphenyl)methyl-2-diphenylmethyl-1-azabicyclo[2.2.2]octan-3-amine, (2S,3S)-2-diphenylmethyl-3-(5-tert-butyl-2-methoxybenzyl)amino-1-azabicyclo[2.2.2]octane;

(2S,3S)-N-[5-(1-cyano-1-methylethyl)-2-methoxybenzyl]-2-phenylpiperidine-3-amine;

(2S,3S)-3-(6-methoxy-1-methyl-2-oxo-1,2,3,4-tetrahydroquinolin-7-yl)methyl-2-phenylpiperidine-3-amine;

(2S,3S)-2-phenyl-N-[5-[2,2,2-trifluoro-1-(trifluoromethyl)ethyl]-2-methoxybenzyl]piperidine-3-amine;

(2S,3S)-2-diphenylmethyl-N-[2-methoxy-5-(methylsulfonyl)benzyl]-1-azabicyclo[2.2.2]octane-3-amine;

(2S,3S)-2-diphenylmethyl-N-(5-isopropenyl-2-methoxybenzyl)-1-azabicyclo[2.2.2]octane-3-amine;

(2S,3S)-2-diphenylmethyl-N-[5-(1-hydroxy-1-methylethyl)-2-methoxybenzyl]-1-azabicyclo[2.2.2]octane-3-amine;

(3R,4S,5S,6S)-N,N-diethyl-5-(5-isopropyl-2-methoxy-benzylamino)-6-diphenylmethyl-1-azabicyclo[2.2.2]octane-3-carboxamide;

(3R,4S,5S,6S)-N,N-diethyl-5-(2,5-dimethoxybenzylamino)-6-diphenylmethyl-1-azabicyclo[2.2.2]octane-3-carboxamide;

(3R,4S,5S,6S)-5-(5-isopropyl-2-methoxybenzylamino)-6-diphenylmethyl-1-azabicyclo[2.2.2]octane-3-carboxylic acid;

(3R,4S,5S,6S)-5-(2-methoxy-2-methylthiobenzylamino)-6-diphenylmethyl-1-azabicyclo[2.2.2]octane-3-carboxylic acid;

(3R,4S,5S,6S)-5-(2,5-dimethoxybenzylamino)-6-diphenylmethyl-1-azabicyclo[2.2.2]octane-3-carboxylic acid;

(3R,4S,5S,6S)-5-(2-methoxy-5-methylbenzylamino)-6-diphenylmethyl-1-azabicyclo[2.2.2]octane-3-carboxylic acid;

(3R,4S,5S,6S)-5-(5-ethyl-2-methoxybenzylamino)-6-diphenylmethyl-1-azabicyclo[2.2.2]octane-3-carboxylic acid;

(3R,4S,5S,6S)-5-(2-methoxyl-5-n-propylbenzylamino)-6-diphenylmethyl-1-azabicyclo[2.2.2]octane-3-carboxylic acid;

(3R,4S,5S,6S)-5-(5-sec-butyl-2-methoxybenzylamino)-6-diphenylmethyl-1-azabicyclo[2.2.2]octane-3-carboxylic acid;

(3R,4S,5S,6S)-5-(5-N-methyl-methanesulfonylamino-2-methoxy-benzylamino)-6-diphenylmethyl-1-azabicyclo[2.2.2]octane-3-carboxylic acid;

(3R,4S,5S,6S)-5-(2-methoxy-5-methylsulfinylbenzyl-amino)-6-diphenylmethyl-1-azabicyclo[2.2.2]octane-3-carboxylic acid;

(3R,4S,5S,6S)-5-(2-methoxy-5-trifluoromethoxybenzyl-amino)-6-diphenylmethyl-1-azabicyclo[2.2.2]octane-3-carboxylic acid;

(3R,4S,5S,6S)-5-(2-methoxy-5-methylsulfonylbenzyl-amino)-6-diphenylmethyl-1-azabicyclo[2.2.2]octane-3-carboxylic acid;

(3R,4S,5S,6S)-5-(5-dimethylamino-2-methoxybenzylamino)-6-diphenylmethyl-1-azabicyclo[2.2.2]octane-3-carboxylic acid;

(3R,4S,5S,6S)-5-(5-isopropyl-2-methoxybenzylamino)-6-diphenylmethyl-1-azabicyclo[2.2.2]octane-2-carboxylic acid;

(3R,4S,5S,6S)-5-(2-methoxy-5-methylthiobenzylamino)-6-diphenylmethyl-1-azabicyclo[2.2.2]octane-2-carboxylic acid;

(3R,4S,5S,6S)-5-(2,5-dimethoxybenzylamino)-6-diphenylmethyl-1-azabicyclo[2.2.2]octane-2-carboxylic acid;

(3R,4S,5S,6S)-5-(2-methoxy-5-methylbenzylamino)-6-diphenylmethyl-1-azabicyclo[2.2.2]octane-2-carboxylic acid;

(3R,4S,5S,6S)-5-(5-ethyl-2-methoxybenzylamino)-6-diphenylmethyl-1-azabicyclo[2.2.2]octane-2-carboxylic acid;

(3R,4S,5S,6S)-5-(2-methoxyl-5-n-propylbenzylamino)-6-diphenylmethyl-1-azabicyclo[2.2.2]octane-2-carboxylic acid;

(3R,4S,5S,6S)-5-(5-sec-butyl-2-methoxybenzylamino)-6-diphenylmethyl-1-azabicyclo[2.2.2]octane-2-carboxylic acid;

(3R,4S,5S,6S)-5-(5-N-methyl-methanesulfonylamino-2-methoxybenzyl-amino)-6-diphenylmethyl-1-azabicyclo[2.2.2]octane-2-carboxylic acid;

(3R,4S,5S,6S)-5-(2-methoxy-5-methylsulfinylbenzyl-amino)-6-diphenylmethyl-1-azabicyclo[2.2.2]octane-2-carboxylic acid;

(3R,4S,5S,6S)-5-(2-methoxy-5-trifluoromethoxybenzyl-amino)-6-diphenylmethyl-1-azabicyclo[2.2.2]octane-2-carboxylic acid;

(3R,4S,5S,6S)-5-(2-methoxy-5-methylsulfonylbenzyl-amino)-6-diphenylmethyl-1-azabicyclo[2.2.2]octane-2-carboxylic acid; and (3R,4S,5S,6S)-5-(5-dimethylamino-2-methoxybenzylamino)-6-diphenylmethyl-1-azabicyclo[2.2.2]octane-2-carboxylic acid;

and the pharmaceutically acceptable salts of the foregoing compounds.

6. A method according to claim 1 wherein the NK-1 receptor antagonist employed is selected from the group consisting of (2S,3S)-2-phenyl-3-[2-methoxyphenyl)methylamino]piperidine; (2S,3S)-3-(5-tert-butyl-2-methoxybenzyl)amino-2-(3-trifluoromethoxyphenyl)piperidine; (2S,3S)-3-(2-methoxy-5-trifluoromethoxybenzyl)-amino-2-phenylpiperidins; (2S,3S)-3-(2-methoxybenzylamino)-2-phenylpiperidine; (2S,3S-3-(5-tertbutyl-2-trifluoromethoxybenzyl)amino-2-phenylpiperidine; cis-3-(2-chlorobenzylamino)-2-phenylpiperidine; (2S,3S)-2-diphenylmethyl-3-(5-tert-butyl-2-methoxybenzyl)amino-1-azabicyclo[2.2.2]octane; cis-3(3,5-difluoro-2-methoxybenzylamino(-2-phenyl-piperidine; 3-(2-methoxybenzylamino)2,4-diphenylpiperidine; (3R,4S,5S,6S)-5-(5-isopropyl-2-methoxybenzylamino)-6-diphenyl-1-azabicyclo[2.2.2]octane-3-carboxylic acid; cis-3-(2-methoxybenzylamino)-2-phenylpyrrolidine; 2,4-dimethylthiazole-5-sulfonic acid[4-isopropxy-3-(2S,3S)-2-phenylpiperidin-3-ylaminomethyl)phenyl-methylamide; 2,4-dimethylthiazole-5-sulfonic acid [4-isopropxy-3-(2S,3S)-2-phenylpiperidin-3-ylaminomethyl)phenyl-isopropylamide; cis-3-(2-methoxybenzylamino)-2-phenylpiperidine; 3-(2-methoxybenzylamino)-4-methyl-2-phenylpiperidine and (2S,3S)-1-carboethoxypent-1-yl)-3-(2-methoxybenzylamino)-2-phenylpiperidine.

\* \* \* \* \*